US010052273B2

(12) United States Patent
Lalleman et al.

(10) Patent No.: US 10,052,273 B2
(45) Date of Patent: *Aug. 21, 2018

(54) HAIR DYEING METHOD EMPLOYING AT LEAST ONE ORTHO-DIPHENOL, ONE TITANIUM DERIVATIVE AND ONE CARBOXYLIC ACID

(71) Applicant: L'OREAL, Paris (FR)

(72) Inventors: Boris Lalleman, Paris (FR); Alain LaGrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/104,131

(22) PCT Filed: Dec. 10, 2014

(86) PCT No.: PCT/EP2014/077225
§ 371 (c)(1),
(2) Date: Jun. 13, 2016

(87) PCT Pub. No.: WO2015/086678
PCT Pub. Date: Jun. 18, 2015

(65) Prior Publication Data
US 2016/0317413 A1    Nov. 3, 2016

(30) Foreign Application Priority Data

Dec. 13, 2013 (FR) .................................. 13 62581

(51) Int. Cl.
| | | |
|---|---|---|
| *A61Q 5/10* | (2006.01) | |
| *A61K 8/49* | (2006.01) | |
| *A61K 8/29* | (2006.01) | |
| *A61K 8/34* | (2006.01) | |
| *A61K 8/362* | (2006.01) | |
| *A61K 8/365* | (2006.01) | |
| *A61K 8/97* | (2017.01) | |
| *A61K 8/22* | (2006.01) | |

(52) U.S. Cl.
CPC ............... *A61K 8/498* (2013.01); *A61K 8/22* (2013.01); *A61K 8/29* (2013.01); *A61K 8/347* (2013.01); *A61K 8/362* (2013.01); *A61K 8/365* (2013.01); *A61K 8/97* (2013.01); *A61Q 5/10* (2013.01); *A61K 2800/4324* (2013.01); *A61K 2800/884* (2013.01)

(58) Field of Classification Search
CPC . A61Q 5/10; A61K 8/29; A61K 8/347; A61K 8/365; A61K 8/97; A61K 8/22; A61K 8/498; A61K 8/362; A61K 2800/884; A61K 2800/4324
See application file for complete search history.

(56) References Cited

U.S. PATENT DOCUMENTS

| | | |
|---|---|---|
| 3,376,110 A | 4/1968 | Shiraeff |
| 4,823,985 A | 4/1989 | Grollier et al. |
| 5,008,093 A | 4/1991 | Merianos |
| 5,183,901 A | 2/1993 | Login et al. |
| 7,081,485 B2 | 7/2006 | Suh et al. |
| 7,833,290 B2 | 11/2010 | Guerin et al. |
| 2003/0103917 A1 | 6/2003 | Pruche |
| 2003/0163878 A1 | 9/2003 | Pruche |
| 2008/0233068 A1 | 9/2008 | Forbes et al. |
| 2010/0146718 A1 | 6/2010 | Guerin et al. |
| 2010/0154143 A1* | 6/2010 | Guerin ..................... A61K 8/19 8/424 |
| 2011/0209294 A1* | 9/2011 | Choi ..................... C07F 7/0859 8/550 |
| 2012/0110751 A1* | 5/2012 | Blackburn ............... A61K 8/19 8/421 |
| 2013/0139846 A1 | 6/2013 | Rondot et al. |

FOREIGN PATENT DOCUMENTS

| | | |
|---|---|---|
| DE | 19859721 A1 | 6/2000 |
| EP | 2196188 A2 | 6/2010 |
| EP | 2438900 A1 | 4/2012 |
| FR | 2586913 A1 | 3/1987 |
| FR | 2814943 A1 | 4/2002 |
| FR | 2814945 A1 | 4/2002 |
| FR | 2814946 A1 | 4/2002 |
| FR | 2814947 A1 | 4/2002 |
| FR | 2928086 A1 | 9/2009 |
| FR | 2951374 A1 | 4/2011 |
| FR | 2976793 A1 | 12/2012 |
| FR | 2976797 A1 | 12/2012 |
| WO | 2006/106366 A1 | 10/2006 |

(Continued)

OTHER PUBLICATIONS

STIC Search Report dated Nov. 28, 2016.*
International Search Report for PCT/EP2014/077224, dated Mar. 11, 2015.
International Search Report for PCT/EP2014/077225, dated Mar. 11, 2015.
Non-Final Office Action for copending U.S. Appl. No. 15/104,121, dated Mar. 27, 2017.

(Continued)

*Primary Examiner* — Eisa B Elhilo
(74) *Attorney, Agent, or Firm* — The Marbury Law Group, PLLC

(57) ABSTRACT

The present invention relates to a method for dyeing keratinous fibers, in particular human keratinous fibers, such as the hair, in which the said fibers are treated starting from one or more cosmetic compositions comprising a) one or more ortho-diphenol(s), b) one or more inorganic titanium salt(s) or alkoxytitanium(s), c) one or more acid(s) and d) optionally one or more chemical oxidizing agent(s), such as hydrogen peroxide or one or more hydrogen peroxide generating system(s).

18 Claims, No Drawings

(56) References Cited

FOREIGN PATENT DOCUMENTS

| WO | 2010/135237 A1 | 11/2010 |
| WO | 2011/000892 A2 | 1/2011 |
| WO | 2011/045404 A2 | 4/2011 |
| WO | 2011/086282 A1 | 7/2011 |
| WO | 2011/086284 A1 | 7/2011 |
| WO | 2012/175683 A2 | 12/2012 |
| WO | 2015/086677 A1 | 6/2015 |

OTHER PUBLICATIONS

Final Office Action for copending U.S. Appl. No. 15/104,121, dated Oct. 24, 2017.
Notice of Allowance for copending U.S. Appl. No. 15/104,121, dated Mar. 19, 2018.

* cited by examiner

HAIR DYEING METHOD EMPLOYING AT LEAST ONE ORTHO-DIPHENOL, ONE TITANIUM DERIVATIVE AND ONE CARBOXYLIC ACID

CROSS REFERENCE TO RELATED APPLICATION

This is a national stage application of PCT/EP2014/077225, filed internationally on Dec. 10, 2014, which claims priority to French Application No. 1362581, filed on Dec. 13, 2013, both of which are incorporated by reference herein in their entireties.

The present invention relates to a method for dyeing keratinous fibres, in particular human keratinous fibres, such as the hair, in which the said fibres are treated starting from one or more cosmetic compositions comprising a) one or more ortho-diphenol(s), b) one or more specific compound(s) comprising titanium, c) one or more acid(s) and d) optionally one or more chemical oxidizing agent(s), such as hydrogen peroxide or one or more hydrogen peroxide generating system(s).

It is known to obtain "permanent" colourations with dyeing compositions comprising oxidation dye precursors, generally known as oxidation bases, such as ortho- or para-phenylenediamines, ortho- or para-aminophenols and heterocyclic compounds. These oxidation bases are colourless or weakly coloured compounds which, in combination with oxidizing products, can give rise to coloured compounds by an oxidative condensation process. It is also known that the shades obtained can be varied by combining these oxidation bases with couplers or colouration modifiers, the latter being chosen in particular from aromatic meta-diamines, meta-aminophenols, meta-diphenols and certain heterocyclic compounds, such as indole compounds. This oxidation dyeing method consists in applying, to the keratinous fibres, bases or a mixture of bases and couplers with hydrogen peroxide ($H_2O_2$ or aqueous hydrogen peroxide solution), as oxidizing agent, in leaving to diffuse, and in then rinsing the fibres. The colourations resulting therefrom are permanent, strong and resistant to external agents, in particular to light, bad weather, washing operations, perspiration and rubbing actions.

However, the commercial hair colourings which comprise them generally exhibit the disadvantage of staining the clothes, of resulting in odour and comfort problems, and of damaging the keratinous fibres. This is particularly the case with oxidation dyes.

In the field of dyeing, it is also known to dye keratinous substances, such as the hair or skin, starting from ortho-diphenol compounds in the presence of a metal salt, in particular a manganese (Mn) and/or zinc (Zn) salt. In particular, Patent Applications FR 2 814 943, FR 2 814 945, FR 2 814 946 and FR 2 814 947 propose compositions for dyeing the skin or keratinous fibres, comprising a dye precursor which comprises at least one ortho-diphenol, Mn and/or Zn oxides and salts, alkaline agents of hydrogencarbonate type in a specific Mn, Zn/hydrogencarbonate ratio, and optionally an enzyme. According to these documents, it is possible to obtain colourations of keratinous substances with atmospheric oxygen or any oxygen-generating system.

However, the colourations obtained are not strong enough or intense enough, and/or are not very persistent, in particular in the case of hair fibres.

Moreover, it is known to use metals at acidic pH for the dyeing of keratinous fibres in amounts similar to those employed for dyes using a mordanting process, which consists in preparing the fibres before carrying out the dyeing in order to obtain persistent colours (*Ullmann's Encyclopedia*, "Metal and Dyes", 2005, § 5.1, p. 8).

However, this method generally exhibits the disadvantage of not always respecting the cosmetic quality of the keratinous fibre.

Other documents describe the use of ortho-diphenols in combination with Mn and Zn salts and other metal salts, including titanium salts, and a chemical oxidizing agent (FR 297 673, WO2011/086284, WO2011/086282 and FR 2 951 374).

Nevertheless, improvements should be further introduced, in particular in terms of persistence of the colour with regard to shampooing operations and sweat.

There thus exists a real need to develop dyeing methods which make it possible to obtain colourations which are more powerful and/or persistent starting from ortho-diphenols, in particular starting from natural extracts rich in ortho-diphenols and less aggressive for keratinous fibres. In particular, there exists a need to obtain colourations which satisfactorily withstand external agents (light, bad weather, shampooing operations, sweat) and which are persistent and homogeneous, i.e. which have a weak colouration selectivity between the root and the tip, while remaining strong and/or chromatic.

This(These) aim(s) is(are) achieved by the present invention, which has, as subject-matter, a method for dyeing keratinous fibres, in particular human keratinous fibres, such as the hair, in which the said fibres are treated, in one or more stages, with one or more cosmetic compositions comprising, taken together or separately in the said composition or compositions, the following ingredients:
  a) one or more ortho-diphenol(s);
  b) one or more inorganic titanium salt(s) or one or more alkoxytitanium(s), in particular the titanium of inorganic titanium salt(s) has the oxidation state 2, 3 or 4, denoted Ti(II), Ti(III) or Ti(IV), preferably Ti(III) or Ti(IV);
  c) one or more carboxylic acid(s) of following formula (I) or one of their salts:

in which formula (I):
  A represents a saturated or unsaturated, cyclic or non-cyclic and aromatic or non-aromatic hydrocarbon group, monovalent when n has the value zero or polyvalent when n is greater than or equal to 1, comprising from 1 to 50 carbon atoms which is optionally interrupted by one or more heteroatoms and/or optionally substituted, in particular by one or more hydroxyl groups; preferably, A represents a monovalent ($C_1$-$C_6$)alkyl group or a polyvalent ($C_1$-$C_6$)alkylene group optionally substituted by one or more hydroxyl groups;
  n represents an integer between 0 and 10 inclusive; preferably, n is between 0 and 5, such as between 0 and 2;
  d) optionally, one or more chemical oxidizing agent(s) chosen in particular from hydrogen peroxide or one or more hydrogen peroxide generating system(s);

it being understood that at least one of the compositions employed in the dyeing method is at acidic pH, i.e. less than 7.0, particularly less than 5, more particularly at a pH of between 0 and 4 inclusive, preferably between 0.5 and 3.5, more preferably between 1 and 3.

Preferably, the composition or compositions employed in the method of the invention is(are) aqueous.

Another subject-matter of the invention is a cosmetic composition comprising the ingredients a), b), c) and optionally d) as defined above.

Another subject-matter of the invention relates to a multicompartment device comprising the ingredients a), b), c) and optionally d) distributed in several compartments.

The multicompartment device or "kit" is suitable for implementing the dyeing method according to the invention.

The method according to the invention exhibits the advantage of dyeing human keratinous fibres, with persistent colouration results. In particular, the dyeing method according to the invention makes it possible to result in colourations which are resistant to washing operations, perspiration, sebum and light without detrimentally affecting the fibres. The resistance to perspiration is particularly good. Furthermore, the dyeing method employed makes it possible to induce a satisfactory "uptake" and/or strength of the colouration.

Other subject-matters, characteristics, aspects and advantages of the present invention will become even more clearly apparent on reading the description and examples which follow.

a) The Ortho-Diphenol(s)

In accordance with the present invention, the dyeing method employs one or more ortho-diphenol(s).

The ortho-diphenol(s) can be present in one or more cosmetic composition(s) used during the dyeing method.

The invention relates to one or more ortho-diphenol(s) or mixtures of compounds comprising one or more aromatic rings, at least one of which is a benzene ring substituted by at least two hydroxyl (OH) groups carried by two adjacent carbon atoms of the said benzene group being present in the structure of the ortho-diphenol or ortho-diphenols.

The aromatic ring is more particularly a fused aryl or fused heteroaromatic ring, i.e. optionally comprising one or more heteroatoms, such as benzene, naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline, the said aromatic ring comprising at least two hydroxyl groups carried by two adjacent carbon atoms of the aromatic ring. Preferably, the aromatic ring of the ortho-diphenol derivatives according to the invention is a benzene ring.

"Fused ring" is understood to mean that at least two saturated or unsaturated and heterocyclic or non-heterocyclic rings exhibit a shared bond, that is to say that at least one ring is placed side-by-side with another ring.

The ortho-diphenols according to the invention may or may not be salified. They can also be in the aglycone form (without bonded sugar) or in the form of glycosylated compounds.

More particularly, the ortho-diphenol or ortho-diphenols a) represents a compound of formula (II), or one of its oligomers, tautomers, optical isomers or geometrical isomers, and also its salts or its solvates, such as the hydrates:

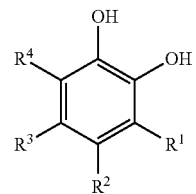

(II)

in which formula (II):

R$^1$ to R$^4$, which are identical or different, represent: i) a hydrogen atom, ii) a halogen atom, or group chosen from iii) hydroxyl, iv) carboxyl, v) (C$_1$-C$_{20}$)alkyl carboxylate or (C$_1$-C$_{20}$)alkoxycarbonyl, vi) optionally substituted amino, vii) optionally substituted linear or branched (C$_1$-C$_{20}$)alkyl, viii) optionally substituted linear or branched (C$_2$-C$_{20}$)alkenyl, ix) optionally substituted cycloalkyl, x) (C$_1$-C$_{20}$)alkoxy, xi) (C$_1$-C$_{20}$)alkoxy(C$_1$-C$_{20}$)alkyl, xii) (C$_1$-C$_{20}$)alkoxyaryl, xiii) aryl which can optionally be substituted, xiv) aryl, xv) substituted aryl, xvi) heterocyclic which is saturated or unsaturated, which carries or does not carry a cationic or anionic charge and which is optionally substituted and/or optionally condensed with an aromatic ring, preferably a benzene ring, the said aromatic ring optionally being substituted, in particular by one or more hydroxyl or glycosyloxy groups, xvii) a radical comprising one or more silicon atoms;

or two of the substituents carried by two adjacent carbon atoms R$^1$-R$^2$, R$^2$-R$^3$ or R$^3$-R$^4$ form, together with the carbon atoms carrying them, a saturated or unsaturated and aromatic or non-aromatic ring optionally comprising one or more heteroatoms and optionally fused with one or more saturated or unsaturated rings optionally comprising one or more heteroatoms. In particular, the compound of formula (II) comprises from one to four rings.

A specific embodiment of the invention relates to one or more ortho-diphenol(s) of formula (II), two adjacent substituents R$^1$-R$^2$, R$^2$-R$^3$ or R$^3$-R$^4$ of which cannot form, with the carbon atoms which carry them, a pyrrolyl radical. According to an alternative form, R$^2$ and R$^3$ form a pyrrolyl or pyrrolidinyl radical fused to the benzene ring carrying the two hydroxyls.

Within the meaning of the present invention and unless otherwise indicated:

the saturated or unsaturated and optionally fused rings can also be optionally substituted;

the "alkyl" radicals are saturated, linear or branched, generally C$_1$-C$_{20}$, particularly C$_1$-C$_{10}$, hydrocarbon radicals, preferably C$_1$-C$_6$ alkyl radicals, such as methyl, ethyl, propyl, butyl, pentyl and hexyl;

the "alkenyl" radicals are unsaturated and linear or branched C$_2$-C$_{20}$ hydrocarbon radicals preferably comprising at least one double bond, such as ethylene, propylene, butylene, pentylene, 2-methylpropylene and decylene;

the "aryl" radicals are monocyclic or fused or non-fused polycyclic carbon-based radicals preferably comprising from 6 to 30 carbon atoms, at least one ring of which is aromatic; the choice is preferably made, from the aryl radical, of a phenyl, biphenyl, naphthyl, indenyl, anthracenyl and tetrahydronaphthyl;

the "alkoxy" radicals are alkyl-oxy radicals with alkyl as defined above, preferably $C_1$-$C_{10}$ alkyl, such as methoxy, ethoxy, propoxy and butoxy;

the "alkoxyalkyl" radicals are ($C_1$-$C_{20}$)alkoxy($C_1$-$C_{20}$) alkyl radicals, such as methoxymethyl, ethoxymethyl, methoxyethyl, ethoxyethyl, and the like;

the "cycloalkyl" radicals are $C_4$-$C_8$ cycloalkyl radicals, preferably the cyclopentyl and cyclohexyl radicals; the cycloalkyl radicals can be substituted cycloalkyl radicals, in particular substituted by alkyl, alkoxy, carboxylic acid, hydroxyl, amine and ketone groups;

the "alkyl" or "alkenyl" radicals, when they are "optionally substituted", can be substituted by at least one atom or group carried by at least one carbon atom chosen from: i) halogen; ii) hydroxyl; iii) ($C_1$-$C_2$)alkoxy; iv) ($C_1$-$C_{10}$)alkoxycarbonyl; v) (poly)hydroxy($C_2$-$C_4$) alkoxy; vi) amino; vii) 5- or 6-membered heterocycloalkyl; viii) optionally cationic 5- or 6-membered heteroaryl, preferably imidazolium, optionally substituted by a ($C_1$-$C_4$)alkyl radical, preferably methyl; ix) amino substituted by one or two identical or different $C_1$-$C_6$ alkyl radicals optionally carrying at least: a) one hydroxyl group, b) one amino group optionally substituted by one or two optionally substituted ($C_1$-$C_3$)alkyl radicals, it being possible for the said alkyl radicals to form, with the nitrogen atom to which they are attached, a saturated or unsaturated and optionally substituted 5- to 7-membered heterocycle optionally comprising at least one other heteroatom different or not different from nitrogen, c) one quaternary ammonium group —$N^+R'R''R'''$ $M^-$ for which R', R'' and R''', which are identical or different, represent a hydrogen atom or a $C_1$-$C_4$ alkyl group and NY represents the counterion of the corresponding organic acid, inorganic acid or halide, d) or one optionally cationic 5- or 6-membered heteroaryl radical, preferably imidazolium, optionally substituted by a ($C_1$-$C_4$)alkyl radical, preferably methyl; x) acylamino (—N(R)—C(O)—R') in which the R radical is a hydrogen atom or a ($C_1$-$C_4$)alkyl radical optionally carrying at least one hydroxyl group and the R' radical is a $C_1$-$C_2$ alkyl radical; a carbamoyl ((R)$_2$N—C(O)—) radical in which the R radicals, which are identical or different, represent a hydrogen atom or a ($C_1$-$C_4$)alkyl radical optionally carrying at least one hydroxyl group; xi) alkylsulfonylamino (R'—S(O)$_2$—N(R)—) in which the R radical represents a hydrogen atom or a ($C_1$-$C_4$)alkyl radical optionally carrying at least one hydroxyl group and the R' radical represents a ($C_1$-$C_4$)alkyl radical, a phenyl radical; xii) aminosulfonyl ((R)$_2$N—S(O)$_2$—) in which the R radicals, which are identical or different, represent a hydrogen atom or a ($C_1$-$C_4$)alkyl radical optionally carrying at least one group chosen from a) hydroxyl, b) carboxyl —C(O)—OH in the acid or salified form (preferably salified with an alkali metal or a substituted or unsubstituted ammonium); xiii) cyano; xiv) nitro; xv) carboxyl or glycosylcarbonyl; xvi) phenylcarbonyloxy optionally substituted by one or more hydroxyl groups; xvii) glycosyloxy; and phenyl group optionally substituted by one or more hydroxyl groups;

the "aryl" or "heterocyclic" radicals or the aryl or heterocyclic part of the radicals, when they are "optionally substituted", can be substituted by at least one atom or group carried by at least one carbon atom chosen from:
i) ($C_1$-$C_{10}$)alkyl, preferably $C_1$-$C_8$ alkyl, optionally substituted by one or more radicals chosen from the following radicals: hydroxyl, ($C_1$-$C_2$)alkoxy, (poly)hydroxy($C_2$-$C_4$)alkoxy, acylamino, amino substituted by two identical or different $C_1$-$C_4$ alkyl radicals optionally carrying at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another heteroatom identical to or different from nitrogen; ii) halogen; iii) hydroxyl; iv) $C_1$-$C_2$ alkoxy; v) $C_1$-$C_{10}$ alkoxycarbonyl; vi) (poly)hydroxy ($C_2$-$C_4$)alkoxy; vii) amino; viii) 5- or 6-membered heterocycloalkyl; ix) optionally cationic 5- or 6-membered heteroaryl, preferably imidazolium, optionally substituted by a ($C_1$-$C_4$)alkyl radical, preferably methyl; x) amino substituted by one or two identical or different $C_1$-$C_6$ alkyl radicals optionally carrying at least: a) one hydroxyl group, b) one amino group optionally substituted by one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom different or not different from nitrogen, c) one quaternary ammonium group —$N'R'R''R'''$ $M^-$ for which R', R'' and R''', which are identical or different, represent a hydrogen atom or a $C_1$-$C_4$ alkyl group and $M^-$ represents the counterion of the corresponding organic acid, inorganic acid or halide, d) or one optionally cationic 5- or 6-membered heteroaryl radical, preferably imidazolium, optionally substituted by a ($C_1$-$C_4$)alkyl radical, preferably methyl; xi) acylamino (—N(R)—C(O)—R') in which the R radical is a hydrogen atom or a $C_1$-$C_4$ alkyl radical optionally carrying at least one hydroxyl group and the R' radical is a $C_1$-$C_2$ alkyl radical; xii) carbamoyl ((R)$_2$N—C(O)—) in which the R radicals, which are identical or different, represent a hydrogen atom or a $C_1$-$C_4$ alkyl radical optionally carrying at least one hydroxyl group; xiii) alkylsulfonylamino (R'S(O)$_2$—N(R)—) in which the R radical represents a hydrogen atom or a $C_1$-$C_4$ alkyl radical optionally carrying at least one hydroxyl group and the R' radical represents a $C_1$-$C_4$ alkyl radical, a phenyl radical; xiv) aminosulfonyl ((R)$_2$N—S(O)$_2$—) in which the R radicals, which are identical or different, represent a hydrogen atom or a $C_1$-$C_4$ alkyl radical optionally carrying at least one hydroxyl group; xv) carboxyl in the acid or salified form (preferably salified with an alkali metal or a substituted or unsubstituted ammonium); xvi) cyano; xvii) nitro; xviii) polyhaloalkyl, preferably trifluoromethyl; xix) a glycosylcarbonyl; xx) a phenylcarbonyloxy group optionally substituted by one or more hydroxyl groups; xxi) a glycosyloxy group; and xxii) a phenyl group optionally substituted by one or more hydroxyl groups;

"glycosyl" radical is understood to mean, within the meaning of the present invention, a radical resulting from a mono- or polysaccharide;

the radicals "comprising one or more silicon atoms" are preferably polydimethylsiloxane, polydiphenylsiloxane, polydimethylphenylsiloxane or stearoxy dimethicone radicals;

the "heterocyclic" radicals are radicals comprising, in at least one ring, one or more heteroatoms chosen in particular from O, N and S, preferably O or N, optionally substituted by in particular one or more alkyl, alkoxy, carboxyl, hydroxyl, amine or ketone groups.

These rings can comprise one or more oxo groups on the carbon atoms of the heterocycle; mention may in particular be made, among the heterocyclic radicals which can be used, of the furyl, pyranyl, pyrrolyl, imidazolyl, pyrazolyl, pyridyl or thienyl groups; more preferably still, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular by one or more OH groups.

The ortho-diphenol(s) of use in the method of the invention can be natural or synthetic. The natural ortho-diphenols include the compounds which may be present in nature and which are reproduced by chemical (semi)synthesis.

The salts of the ortho-diphenols of the invention can be salts of acids or of bases. The acids can be inorganic or organic. Preferably, the acid is hydrochloric acid, which results in chlorides.

"Basifying agents" is understood to mean the bases as defined for e) can be inorganic or organic. In particular, the bases are alkali metal hydroxides, such as sodium hydroxide, which results in sodium salts.

According to a specific embodiment of the invention, the composition comprises, as ingredient a), one or more synthetic ortho-diphenol(s) which do not exist in nature.

According to another preferred embodiment of the invention, the composition of use in the method for dyeing keratinous fibres comprises, as ingredient a), one or more natural ortho-diphenol(s).

More particularly, the ortho-diphenol(s) which can be used in the method of the invention according to a) (is)are in particular:
flavanols, such as catechin and epicatechin gallate,
flavonols, such as quercetin,
anthocyanidins, such as cyanidin, delphinidin or petunidin,
anthocyanins or anthocyans, such as myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and its derivatives,
2,3-dihydroxyphenylalanine and its derivatives,
4,5-dihydroxyphenylalanine and its derivatives,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
quinones,
hydroxyxanthones,
1,2-dihydroxybenzene and its derivatives,
1,2,4-trihydroxybenzene and its derivatives,
1,2,3-trihydroxybenzene and its derivatives,
2,4,5-trihydroxytoluene and its derivatives,
proanthocyanidins and in particular the proanthocyanidins A1, A2, B1, B2, B3 and C1,
chroman and chromene compounds,
proanthocyanins,
tannic acid,
ellagic acid,
and the mixtures of the preceding compounds.

"Chromene or chroman" ortho-diphenol compounds are understood to mean, according to the invention, ortho-diphenols which comprise, in their structure, at least one bicycle of following formula (A):

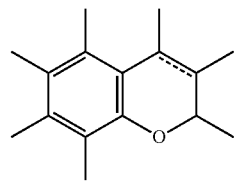

(A)

the intracyclic bond ---- representing a carbon-carbon single bond or else a carbon-carbon double bond, as illustrated by the formula (A1) below, denoting the chromene family, and the formula (A2) below, denoting the chroman family:

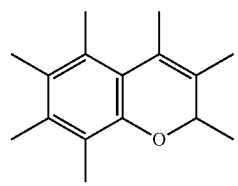

(A1)

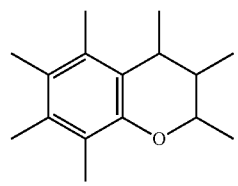

(A2)

More particularly, the ortho-diphenols of the invention are of formula (A) and are preferably chosen from the dyes of following formulae:
formula (III), comprising, in its structure, the bicycle of formula (A2):

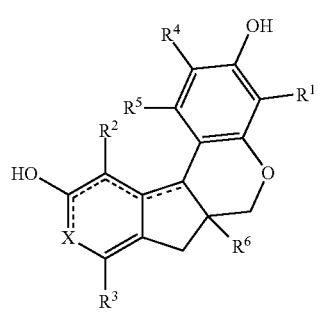

(III)

and also its tautomeric and/or mesomeric forms, its stereoisomers, its addition salts with a cosmetically acceptable acid or base, and its hydrates; in which formula (III):
---- represents a carbon-carbon single bond or a carbon-carbon double bond, the sequence of these ---- bonds denoting two carbon-carbon single bonds and two carbon-carbon double bonds, the said bonds being conjugated, X represents a group:

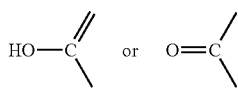

R$^1$, R$^2$, R$^3$, R$^4$, R$^5$ and R$^6$, which are identical or different, represent a hydrogen atom, a hydroxyl group, an optionally substituted alkyl group, an optionally substituted alkoxy group or an optionally substituted acyloxy group; and)

formula (IV), comprising, in its structure, the bicycle of formula (A1):

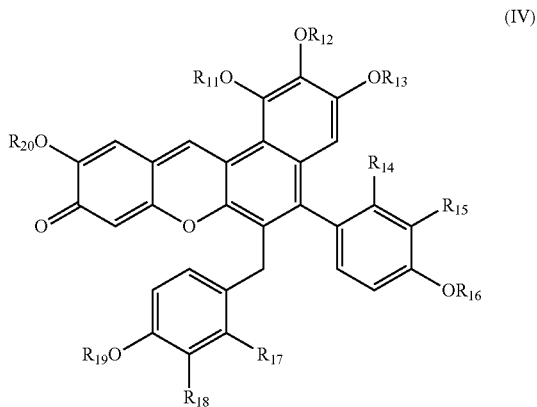

and also its tautomeric and/or mesomeric forms, its stereoisomers, its addition salts with a cosmetically acceptable acid or base, and its hydrates; in which formula (IV):

R$_{11}$, R$_{12}$, R$_{13}$, R$_{16}$, R$_{19}$ and R$_{20}$, which are identical or different, represent a hydrogen atom or a C$_1$-C$_4$ alkyl radical, and R$_{14}$, R$_{15}$, R$_{17}$ and R$_{18}$, which are identical or different, represent a hydrogen atom, a hydroxyl radical or a C$_1$-C$_4$ alkoxy radical.

As regards the ortho-diphenols of formula (III) as defined above, these can occur in two tautomeric forms denoted (IIIa) and (IIIb):

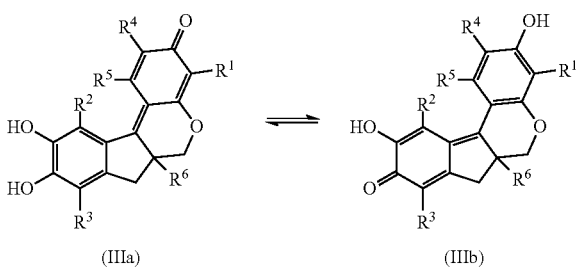

The alkyl radicals mentioned in the preceding definitions of the substituents are saturated and linear or branched hydrocarbon radicals, generally C$_1$-C$_{20}$, particularly C$_1$-C$_{10}$, preferably C$_1$-C$_6$, hydrocarbon radicals, such as methyl, ethyl, propyl, butyl, pentyl and hexyl.

The alkoxy radicals are alkyl-oxy radicals with the alkyl radicals as defined above and preferably the alkoxy radicals are C$_1$-C$_{10}$ alkoxy radicals, such as methoxy, ethoxy, propoxy and butoxy.

The alkyl or alkoxy radicals, when they are substituted, can be substituted by at least one substituent carried by at least one carbon atom chosen from: i) a halogen atom or ii) a hydroxyl group; iii) a C$_1$-C$_2$ alkoxy group; iv) a C$_1$-C$_{10}$ alkoxycarbonyl group; v) a (poly)hydroxy(C$_2$-C$_4$)alkoxy group; vi) an amino group; vii) a 5- or 6-membered heterocycloalkyl group; viii) an optionally cationic 5- or 6-membered heteroaryl group, preferably imidazolium, optionally substituted by a (C$_1$-C$_4$)alkyl radical, preferably methyl; ix) an amino radical substituted by one or two identical or different C$_1$-C$_6$ alkyl radicals optionally carrying at least: a) one hydroxyl group, b) one amino group optionally substituted by one or two optionally substituted C$_1$-C$_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom different or not different from nitrogen, c) one quaternary ammonium group —N$^+$R'R''R''' M$^-$ for which R', R'' and R''', which are identical or different, represent a hydrogen atom or a C$_1$-C$_4$ alkyl group and M$^-$ represents the counterion of the corresponding organic acid, inorganic acid or halide, d) or one optionally cationic 5- or 6-membered heteroaryl radical, preferably imidazolium, optionally substituted by a (C$_1$-C$_4$)alkyl radical, preferably methyl; x) an acylamino (—NR—COR') radical in which the R radical is a hydrogen atom or a C$_1$-C$_4$ alkyl radical optionally carrying at least one hydroxyl group and the R' radical is a C$_1$-C$_2$ alkyl radical; xi) a carbamoyl ((R)$_2$N—CO—) radical in which the R radicals, which are identical or different, represent a hydrogen atom or a C$_1$-C$_4$ alkyl radical optionally carrying at least one hydroxyl group; xii) an alkylsulfonylamino (R'S(O)$_2$—NR—) radical in which the R radical represents a hydrogen atom or a C$_1$-C$_4$ alkyl radical optionally carrying at least one hydroxyl group and the R' radical represents a C$_1$-C$_4$ alkyl radical, a phenyl radical; xiii) an aminosulfonyl ((R)$_2$N—SO$_2$—) radical in which the R radicals, which are identical or different, represent a hydrogen atom or a C$_1$-C$_4$ alkyl radical optionally carrying at least one hydroxyl group; xiv) a carboxyl radical in the acid or salified form (preferably salified with an alkali metal or a substituted or unsubstituted ammonium); xv) a cyano group; xvi) a nitro group; xvii) a carboxyl or glycosylcarbonyl group; xviii) a phenylcarbonyloxy group optionally substituted by one or more hydroxyl groups; xix) a glycosyloxy group; and xx) a phenyl group optionally substituted by one or more hydroxyl groups.

Glycosyl radical is understood to mean a radical resulting from a mono- or polysaccharide.

Preferably, the alkyl or alkoxy radicals of formula (I) are unsubstituted.

According to a specific embodiment of the invention, the dyes of formula (I) comprise an R$_6$ radical representing a hydroxyl group.

Another specific embodiment of the invention relates to the ortho-diphenols of formula (III) for which the R$_1$ radical represents a hydrogen atom or a hydroxyl group.

More particularly, the composition according to the invention can comprise one or more ortho-diphenol(s) of formula (III) chosen from haematoxylin, haematein, brazilin and brazilein.

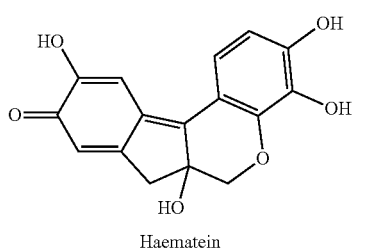

Haematein

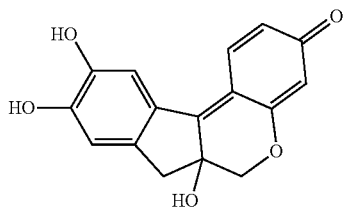

Brazilein

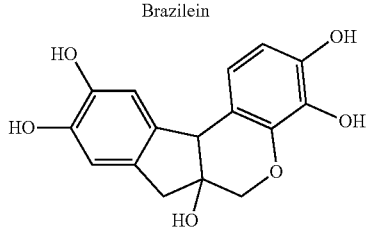

Haematoxylin
(Natural Black 1-CAS 517-28-2)

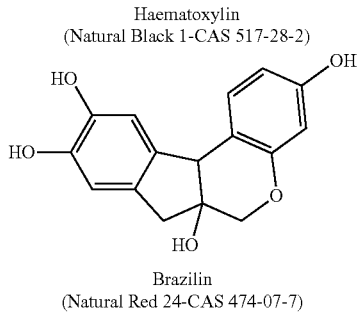

Brazilin
(Natural Red 24-CAS 474-07-7)

Brazilein is a conjugated form of a chroman compound of formula (A2). The tautomeric structures (IIIa) and (IIIb) illustrated above are found in the scheme below.

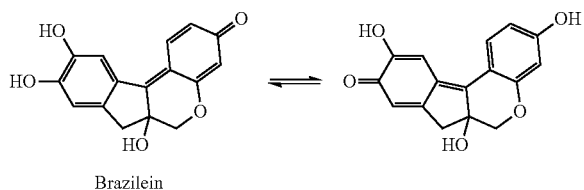 [SMILES: O=C1C=CC2=C3c4cc(O)c(O)cc4CC3(O)COC2=C1 ; O=C1C=C2CC3(O)COc4cc(O)ccc4C3=C2C=C1O]

Brazilein

Mention may be made, among the ortho-diphenols of haematoxylin/haematein and brazilin/brazilein type, by way of example, of haematoxylin (Natural Black 1 according to the INCl name) and brazilin (Natural Red 24 according to the INCl name), dyes of the indochroman family, which are commercially available. These can exist in an oxidized form and be obtained synthetically or by way of extraction of plants or vegetables known to be rich in these dyes.

The ortho-diphenols of formula (III) can be used in the form of extracts. Use may be made of the following plant extracts (genus and species): *Haematoxylon campechianum,* *Haematoxylon brasiletto, Caesalpinia echinata, Caesalpinia sappan, Caesalpinia spinosa* and *Caesalpinia brasiliensis.*

The extracts are obtained by extraction of various plant parts, such as, for example, the root, wood, bark or leaves.

According to a specific embodiment of the invention, natural ortho-diphenols of formula (I) are obtained from logwood, Pernambuco wood, sappan wood and Brazilwood.

As regards the ortho-diphenols of formula (IV), the ortho-diphenols used in the present invention are preferably those for which $R_{11}$ and $R_{13}$ represent an alkyl radical, preferably methyl.

Preferably, $R_{12}$, $R_{16}$, $R_{19}$ and $R_{20}$ denote, independently of one another, a hydrogen atom or an alkyl radical, preferably methyl.

Preferably, $R_{14}$ and $R_{17}$ denote, independently of one another, a hydrogen atom or an alkoxy radical, preferably methoxy.

Preferably, $R_{18}$ and $R_{15}$ denote, independently of one another, a hydrogen atom, a hydroxyl radical or an alkoxy radical, preferably methoxy.

A first particularly preferred family of ortho-diphenols suitable for the present invention is that of the dyes corresponding to the formula (II) above for which $R_{12}$, $R_{15}$, $R_{16}$, $R_{17}$, $R_{19}$ and $R_{20}$ each represent a hydrogen atom. $R_{11}$ and $R_{13}$ each represent a methyl radical and $R_{14}$ represents a methoxy radical.

The preferred ortho-diphenols of this first family include those for which $R_{18}$ represents a methoxy radical (santalin B) or a hydroxyl radical (santalin A).

A second particularly preferred family of ortho-diphenols suitable for the present invention is that of the dyes corresponding to the formula (IV) above for which:
$R_{11}$ and $R_{13}$ each represent a methyl radical,
$R_{17}$ represents a methoxy radical.

A preferred dye of this second family is that for which, in addition, $R_{19}$ represents a methyl radical, $R_{20}$, $R_{12}$, $R_{14}$, $R_{18}$ and $R_{16}$ each represent a hydrogen atom and $R_{15}$ represents the hydroxyl radical (santarubin A).

A second preferred dye of this second family is that for which $R_{18}$, $R_{20}$, $R_{12}$, $R_{14}$ and $R_{16}$ represent a hydrogen atom, $R_{15}$ represents a methoxy radical and $R_{19}$ represents a methyl radical (santarubin B).

A third preferred dye of this second family is that for which $R_{20}$, $R_{12}$, $R_{14}$, $R_{15}$, $R_{16}$ and $R_{19}$ represent hydrogen and $R_{18}$ represents the hydroxyl radical (santarubin C).

Another preferred ortho-diphenol of this second family is that for which $R_{15}$ represents a methoxy radical, $R_{18}$ and $R_{14}$ represent a hydrogen atom and $R_{20}$, $R_{12}$, $R_{16}$ and $R_{19}$ represent a methyl radical (tetra-O-methylsantarubin).

The ortho-diphenols of formula (IV) can be used in the form of extracts. Use may be made of plant extracts of red woods, bringing together generally the species of red woods from Asia and West Africa of the genus *Pterocarpus* and of the genus *Baphia*. These woods are, for example, *Pterocarpus santalinus, Pterocarpus osun, Pterocarpus soyauxii, Pterocarpus erinaceus, Pterocarpus indicus* or *Baphia nitida*. These woods can also be called padauk, sandalwood, narra wood, camwood or bar wood.

Thus, extracts which can be used, comprising ortho-diphenols of formula (II), in the present invention can, for example, be obtained from red sandalwood (*Pterocarpus santalinus*) by aqueous basic extraction, such as the product sold under the trade name Santal Còncentré SL 709C by COPIAA, or also by means of solvent extraction of sandalwood powder, such as the product sold under the trade name Santal Poudre SL PP by the same company COPIAA.

Mention may also be made of the aqueous/alcoholic extract of powdered red sandalwood from Alban Muller.

Extracts also suitable for the present invention can be obtained from woods such as camwood (*Baphia nitida*) or also bar wood (*Pterocarpus soyauxii, Pterocarpus erinaceus*): the latter is thus split up and then ground: a conventional alcoholic extraction or one by percolation is subsequently carried out on this ground material in order to collect a pulverulent extract particularly suitable for the implementation of the present invention.

The ortho-diphenol salts of formulae (III) and (IV) of the invention can be salts of acids or bases which are cosmetically acceptable.

The acids can be inorganic or organic. Preferably, the acid is hydrochloric acid, which results in chlorides.

The bases can be inorganic or organic. In particular, the bases are alkali metal hydroxides, such as sodium hydroxide, resulting in sodium salts.

Preferably, the ortho-diphenol or ortho-diphenols of formulae (III) and (IV) included in the composition according to the invention result from plant extracts. Use may also be made of mixtures of plant extracts.

The natural extracts of the ortho-diphenols according to the invention can be provided in the form of powders or liquids. Preferably, the extracts are provided in the powder form.

In particular, the ortho-diphenols of the invention are chosen from catechin, quercetin, brazilin, haematein, haematoxylin, chlorogenic acid, caffeic acid, gallic acid, catechol, L-DOPA, pelargonidin, cyanidin, (−)-epicatechin, (−)-epigallocatechin, (−)-epigallocatechin 3-gallate (EGCG), (+)-catechin, isoquercetin, pomiferin, esculetin, 6,7-dihydroxy-3-(3-hydroxy-2,4-dimethoxyphenyl)coumarin, santalin AC, mangiferin, butein, maritimetin, sulfuretin, robtein, betanidin, pericampylinone A, theaflavin, proanthocyanidin A2, proanthocyanidin B2, proanthocyanidin C1, procyanidins DP 4-8, tannic acid, purpurogallin, 5,6-dihydroxy-2-methyl-1,4-naphthoquinone, alizarin, wedelolactone, variegatic acid, gomphidic acid, xerocomic acid, carnosol and the natural extracts comprising them.

Preferably, the ortho-diphenols of the invention are chromenes or chromans and are chosen from haematein, haematoxylin, brazilein, brazilin or santalin A.

"Carboxylate" is understood to mean any carboxylic acid salt.

When the dye precursors exhibit D and L forms, both forms can be used in the compositions according to the invention, as can the racemates.

According to one embodiment, the natural ortho-diphenols result from extracts of animals, bacteria, fungi, algae, plants and fruits, used in their entirety or partially. In particular regarding the plants, the extracts are derived from fruits, including citrus fruits, from vegetables, from trees and from shrubs. Use may also be made of mixtures of these extracts rich in ortho-diphenols as defined above.

Preferably, the natural ortho-diphenol or ortho-diphenols of the invention result from extracts of plants or of plant parts.

Within the meaning of the invention, these extracts will be put into the same category as compounds a).

The extracts are obtained by extraction of various plant parts, such as, for example, the root, the wood, the bark, the leaf, the flower, the fruit, the seed, the pod or the peel.

Mention may be made, among the extracts of plants, of extracts of rose or tea leaves.

Mention may be made, among the extracts of fruit, of extracts of apple, extracts of grape (in particular of grape seed) or extracts of cocoa beans and/or pods.

Mention may be made, among the extracts of vegetables, of extracts of potato or of onion peel.

Mention may be made, among the extracts of tree wood, of extracts of pine bark or extracts of logwood.

Use may also be made of mixtures of plant extracts.

According to a specific embodiment of the invention, the ortho-diphenol derivative or derivatives are natural extracts rich in ortho-diphenols. According to a preferred embodiment, the ortho-diphenol derivative or derivatives are solely natural extracts.

Preferentially, the ortho-diphenol(s) according to the invention is(are) chosen from catechin, quercetin, haematein, haematoxylin, brazilin, brazilein, gallic acid, tannic acid and the natural extracts comprising them chosen from grape marc, pine bark, green tea, onion, cocoa bean, logwood, red wood and oak apple.

More preferably, the ortho-diphenol(s) of the invention is(are) chosen from:
haematein, brazilein, gallic acid or tannic acid, when the dyeing method does not employ a chemical oxidizing agent;
or else
haematoxylin, brazilin, gallic acid or tannic acid, when the dyeing method employs a chemical oxidizing agent.

The natural extracts according to the invention can be provided in the form of powders or liquids. Preferably, the extracts of the invention are provided in the form of powders.

According to the invention, the synthetic or natural ortho-diphenol(s) and/or the natural extract(s) used as ingredient a) in one or more cosmetic composition(s) of use in the method according to the invention preferably represent(s) from 0.001% to 20% by weight of the total weight of the composition or compositions comprising the ortho-diphenol or ortho-diphenols or the extract or extracts.

As regards the pure ortho-diphenols, the content in the composition or compositions comprising them is preferably between 0.001% and 5% by weight of each of these compositions.

As regards the extracts, the content in the composition or compositions comprising the extracts per se is preferably between 0.5% and 20% by weight of each of these compositions.

b) The Compound or Compounds Based on Titanium

According to a specific embodiment, the ingredient b) employed in the composition and method of the invention is at least one inorganic titanium salt.

"Inorganic titanium salt" is understood to mean, within the meaning of the present invention, the salts proper resulting in particular from the action of an inorganic acid on Ti.

"Inorganic acid" is understood to mean an acid which does not comprise carbon atoms, apart from carbonic acid.

The inorganic titanium salts are preferably chosen from titanium halides, titanium sulfates and titanium phosphates. Preferably, the titanium salts are inorganic Ti(II), Ti(III) or Ti(IV) salts.

According to another specific embodiment, the ingredient b) employed in the composition and method of the invention is at least one alkoxytitanium.

Alkoxytitaniums preferably have the following structure $Ti(OR)_n$, with n=2, 3 or 4, preferably 4, and R representing a linear or branched $(C_1$-$C_{10})$alkyl or $(C_2$-$C_{10})$alkenyl group optionally substituted by one or more atoms or groups chosen from halo, hydroxyl or (di)($C_1$-$C_4$)(alkyl)amino.

Mention may be made, as advantageous alkoxytitanium according to the invention, of the isopropyl titanate compound provided by DuPont under the name Tyzor TPT.

The inorganic titanium salt(s) or the alkoxytitanium(s) is(are) present in the cosmetic composition(s) used in the method according to the invention in a content ranging from 0.001% to 20% by weight, with respect to the total weight of the composition or compositions in which they are present.

In particular, the titanium salts or complexes according to the invention are soluble in water in a proportion of at least 0.0001 g/l, better still of at least 1 g/l.

Preferably, the ingredient or ingredients b) are inorganic Ti salts.

c) One or More Carboxylic Acid(s) of Formula (I) or One of Their Salts

The dyeing method of the invention also employs at least one specific carboxylic acid of formula (I) as defined above. More particularly, the carboxylic acid or acids of formula (I) are such that A represents a monovalent ($C_1$-$C_6$)alkyl or polyvalent ($C_1$-$C_6$)alkylene group optionally substituted by one or more hydroxyl groups, and n represents an integer between 0 and 5, such as between 0 and 2, inclusive.

More particularly, the carboxylic acid or acids of the invention are chosen from the acids of formula (I) exhibiting a solubility in water of greater than or equal to 1% by weight at 25° C. and at atmospheric pressure.

Preferably, the acids of formula (I) comprise at least one hydroxyl group in their structure. More preferably still, the acid is chosen from α-hydroxy acids. The preferred acids of the invention are chosen from glycolic acid, lactic acid, tartaric acid or citric acid.

The salts of the acids of formula (I) can be salts of organic or inorganic bases, such as sodium hydroxide, aqueous ammonia or potassium hydroxide, or salts of organic amines, such as alkanolamines. The acids of formula (I) or their salts are present in the composition or compositions comprising them in a content ranging from 0.1% to 20% by weight.

d) A Chemical Oxidizing Agent

According to a specific embodiment of the invention, the dyeing method also employs a chemical oxidizing agent. Chemical oxidizing agent is understood to mean an oxidizing agent other than atmospheric oxygen. More particularly, the dyeing method employs hydrogen peroxide a) urea hydrogen peroxide; b) polymeric complexes which can release hydrogen peroxide, such as polyvinylpyrrolidone/$H_2O_2$, provided in particular in the form of powders, and the other polymeric complexes described in U.S. Pat. No. 5,008,093, U.S. Pat. No. 3,376,110 and U.S. Pat. No. 5,183,901; c) oxidases in the presence of an appropriate substrate (for example, glucose in the case of glucose oxidase or uric acid with uricase); d) metal peroxides which generate hydrogen peroxide in water, such as calcium peroxide or magnesium peroxide; e) perborates; or f) percarbonates.

According to a preferred embodiment of the invention, the composition comprises one or more chemical oxidizing agent(s) chosen from a) urea hydrogen peroxide; b) polymeric complexes which can release hydrogen peroxide chosen from polyvinylpyrrolidone/$H_2O_2$; c) oxidases; e) perborates and f) percarbonates.

In particular, the dyeing method employs hydrogen peroxide.

Moreover, the composition or compositions comprising hydrogen peroxide or a hydrogen peroxide generating system can also include various adjuvants conventionally used in compositions for dyeing keratinous fibres as defined below.

According to a specific embodiment of the invention, the chemical oxidizing agent or agents used preferably represent from 0.001% to 12% by weight of chemical oxidizing agents (of hydrogen peroxide), with respect to the total weight of the composition or compositions comprising it or them, and more preferably still from 0.2% to 2.7% by weight.

e) One or More Basifying Agent(s)

According to a specific embodiment of the invention, the dyeing method employs one or more basifying agent(s). They are base(s) which makes it possible to increase the pH of the composition or compositions in which they are present. The basifying agent is a Bronsted, Lowry or Lewis base. It can be inorganic or organic.

In particular, the said agent is chosen from i) (bi)carbonates, ii) aqueous ammonia, iii) alkanolamines, such as monoethanolamine, diethanolamine, triethanolamine and their derivatives, iv) oxyethylenated and/or oxypropylenated ethylenediamines, v) inorganic or organic hydroxides, vi) alkali metal silicates, such as sodium metasilicates, vii) amino acids, preferably basic amino acids, such as arginine, lysine, ornithine, citrulline and histidine, and viii) the compounds of following formula (V):

in which formula (V) W is a divalent ($C_1$-$C_8$)alkylene radical optionally substituted by at least one hydroxyl group or at least one ($C_1$-$C_4$)alkyl radical and/or optionally interrupted by at least one heteroatom, such as oxygen or sulfur, or by an —N($R_e$)— group; $R_a$, $R_b$, $R_c$, $R_d$ and $R_e$, which are identical or different, represent a hydrogen atom or a ($C_1$-$C_4$)alkyl or hydroxy($C_1$-$C_4$)alkyl radical; preferably, W represents a propylene radical. The inorganic or organic hydroxides are preferably chosen from a) hydroxides of an alkali metal, b) hydroxides of an alkaline earth metal, such as sodium hydroxide or potassium hydroxide, c) hydroxides of a transition metal, such as hydroxides of metals from Groups III, IV, V and VI, d) hydroxides of lanthanides or actinides, quaternary ammonium hydroxides and guanidinium hydroxide.

The hydroxide can be formed in situ, such as, for example, guanidine hydroxide, by reaction of calcium hydroxide and guanidine carbonate.

(Bi)carbonates i) is understood to mean:
a) carbonates of alkali metals ($Met_2^+$ $CO_3^{2-}$), of alkaline earth metals ($Met'^{2+}$ $CO_3^{2-}$), of ammonium (($R''_4N^+$)$_2$ $CO_3^{2-}$) or of phosphonium (($R''_4P^+$)$_2$ $CO_3^{2-}$), with Met' representing an alkaline earth metal and Met representing an alkali metal and R", which are identical or different, representing a hydrogen atom or an optionally substituted ($C_1$-$C_6$)alkyl group, such as hydroxyethyl, and
b) bicarbonates, also known as hydrogencarbonates, of following formulae:
R'+ $HCO_3^-$, with R' representing a hydrogen atom, an alkali metal, an ammonium group $R''_4N^+$— or a phosphonium group $R''_4P^+$—, where R", which are identical or different, represent a hydrogen atom or an optionally substituted ($C_1$-$C_6$)alkyl group, such as a hydroxyethyl group, and, when R' represents a hydrogen atom, the hydrogencarbonate is then known as dihydrogencarbonate ($CO_2$, $H_2O$); and Met'$^{2+}$ ($HCO_3$)$_2$, with Met' representing an alkaline earth metal.

More particularly, the basifying agent is chosen from alkali metal or alkaline earth metal (bi)carbonates and amino acids, such as arginine, preferably alkali metal (bi)carbonates and amino acids.

Mention may be made of Na, K, Mg and Ca carbonates or hydrogencarbonates and their mixtures, in particular of sodium hydrogencarbonate. These hydrogencarbonates can originate from a natural water, for example spring water from the Vichy basin or from La Roche-Posay or Badoit water (cf. patent, for example the document FR 2 814 943). Mention may in particular be made of sodium carbonate [497-19-8]=$Na_2CO_3$, sodium hydrogencarbonate or sodium bicarbonate [144-55-8]=$NaHCO_3$, and sodium dihydrogencarbonate=$Na(HCO_3)_2$.

According to a particularly advantageous embodiment, the basifying agent(s) e) is(are) chosen from amino acids, such as arginine, and (bi)carbonates, in particular alkali metal or alkaline earth metal (bi)carbonates, alone or as mixtures. They are preferably found together during the dyeing method.

The basifying agent(s) as defined above preferably represent from 0.001% to 10% by weight of the weight of the composition or compositions comprising them, more particularly from 0.005% to 8% by weight of the composition.

The Water

According to one embodiment of the invention, water is preferably included in the method of the invention. It can originate from the moistening of the keratinous fibres and/or from the composition or compositions comprising the compounds a) to e) as defined above or from one or more other compositions.

Preferably, the water originates from at least one composition comprising at least one compound chosen from a) to e) as defined above.

The Compositions

The compositions according to the invention generally comprise water or a mixture of water and of one or more organic solvents or a mixture of organic solvents.

Organic solvent is understood to mean an organic substance which is capable of dissolving or dispersing another substance without chemically modifying it.

The Organic Solvents

Mention may be made, as organic solvent, for example, of lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether, diethylene glycol monomethyl ether or hexylene glycol; and also aromatic alcohols, such as benzyl alcohol or phenoxyethanol. Preferably, the dyeing composition, i.e. comprising the ortho-diphenol or ortho-diphenols, of the invention comprises at least one organic solvent as defined above and in particular an organic solvent chosen from aromatic alcohols, such as benzyl alcohol.

The organic solvents are present in proportions preferably of between 1% and 40% by weight approximately and more preferably still between 5% and 30% by weight approximately, with respect to the total weight of the dyeing composition.

The Adjuvants

The composition or compositions of the dyeing method in accordance with the invention can also include various adjuvants conventionally used in hair dyeing compositions, such as anionic, cationic, non-ionic, amphoteric or zwitterionic surfactants or their mixtures, anionic, cationic, non-ionic, amphoteric or zwitterionic polymers or their mixtures, inorganic or organic thickening agents and in particular anionic, cationic, non-ionic and amphoteric polymeric associative thickeners, antioxidants, penetrating agents, sequestering agents, fragrances, buffers, dispersing agents, conditioning agents, such as, for example, volatile or non-volatile and modified or unmodified silicones, film-forming agents, ceramides, preservatives or opacifying agents.

The said adjuvants are preferably chosen from surfactants, such as anionic or non-ionic surfactants or their mixtures, and inorganic or organic thickening agents.

The above adjuvants are generally present in an amount for each of them of between 0.01% and 40% by weight, with respect to the weight of the composition, and preferably between 0.1% and 20% by weight, with respect to the weight of the composition.

Of course, a person skilled in the art will take care to choose this or these optional additional compound or compounds so that the advantageous properties intrinsically attached to the composition or to the compositions of use in the dyeing method in accordance with the invention are not, or not substantially, detrimentally affected by the envisioned addition or additions.

The Additional Dyes

The dyeing method employing the ingredients a) to e) as are defined above can furthermore employ one or more additional direct dyes. These direct dyes are chosen, for example, from those conventionally used in direct dyeing, and among which mention may be made of any commonly used aromatic and/or non-aromatic dye, such as neutral, acidic or cationic nitrobenzene direct dyes, neutral, acidic or cationic azo direct dyes, natural direct dyes other than ortho-diphenols, neutral, acidic or cationic quinone and in particular anthraquinone direct dyes, azine, triarylmethane, indoamine, methine, styryl, porphyrin, metalloporphyrin, phthalocyanine and methine cyanine direct dyes, and fluorescent dyes.

Mention may be made, among natural direct dyes, of lawsone, juglone, indigo, isatin, curcumin, spinulosin, apigenidin and orceins. Use may also be made of extracts or decoctions comprising these natural dyes and in particular henna-based poultices or extracts.

According to the invention, the direct dye or dyes used in the composition(s) of the dyeing method according to the invention preferably represent from 0.001% to 10% by weight approximately of the total weight of the composition or compositions and more preferentially still from 0.05% to 5% by weight approximately.

The composition according to the invention or the composition(s) of the method employing the ingredients a) to e) as are defined above can also comprise one or more oxidation bases and/or one or more couplers conventionally used for dyeing keratinous fibres.

Mention may be made, among the oxidation bases, of para-phenylenediamines, bis(phenyl)alkylenediamines, para-aminophenols, bis-para-aminophenols, ortho-aminophenols, heterocyclic bases and their addition salts.

Mention may in particular be made, among these couplers, of meta-phenylenediamines, meta-aminophenols, meta-diphenols, naphthalene couplers, heterocyclic couplers and their addition salts.

The oxidation base(s) present in the said composition(s) which is (are) employed in the method is (are) generally each present in an amount of between 0.001% and 10% by weight of the total weight of the composition(s) comprising it or them.

The cosmetic composition(s) of the invention can be provided in various formulation forms, such as a powder, a lotion, a foam, a cream or a gel, or in any other form appropriate for dyeing keratinous fibres. They can also be packaged in a propellant-free pump-action spray or under pressure in an aerosol container in the presence of a propellant and can form a foam.

pH of the Composition(s)

In accordance with the present invention, the pH of at least one of the cosmetic compositions comprising at least one of the ingredients a), b), c) or d) is acidic, i.e. less than 7.0, particularly less than 5, more particularly at a pH of between 0 and 4 inclusive, preferably between 0.5 and 3.5, more preferably between 1 and 3.

According to one embodiment, the pH of the cosmetic composition or compositions comprising one or more alkaline agents preferably chosen from (bi)carbonates is alkaline, i.e. greater than 7, preferably of between 8 and 12 and more particularly of between 8 and 10.5 inclusive.

Preferably, the composition comprising the ortho-diphenol or ortho-diphenols a) exhibits an acidic pH of less than 7.0, particularly less than 5, more particularly at a pH of between 0 and 4 inclusive, preferably between 0.5 and 3.5, more preferably between 1 and 3.

According to a specific embodiment of the invention, the composition comprising the inorganic titanium salt or salts or the alkoxytitanium or alkoxytitaniums b) and not comprising (bi)carbonates exhibits a pH of less than 7.0, particularly less than 5, more particularly at a pH of between 0 and 4 inclusive, preferably between 0.5 and 3.5, more preferably between 1 and 3.

The pH of these compositions can be adjusted to the desired value by means of basifying agents as defined above in e) or starting from acidifying agents generally used in the dyeing of keratinous fibres, or alternatively using conventional buffer systems. Mention may be made, among the acidifying agents for the compositions used in the invention, as examples, of inorganic or organic acids, such as hydrochloric acid, orthophosphoric acid, sulfuric acid, carboxylic acids, such as acetic acid, tartaric acid, citric acid or lactic acid, or sulfonic acids.

"Carboxylic acid" is understood to mean a compound comprising at least one carboxylic acid —C(O)—OH group, preferably of formula (I) as defined above, preferably comprising between 1 and 4 carboxylic acid groups, such as 1 or 2, or chosen from: i) $(C_1-C_{10})$alkyl-$[C(O)-OH]_n$ and ii) het-$[C(O)-OH]_n$, with n an integer between 1 and 4, preferably between 1 and 2, inclusive and het representing a heterocyclic group, such as pyrrolidone, it being possible for the alkyl or het group to be optionally substituted by one or more groups chosen in particular from OH and $(di)(C_1-C_6)$(alkyl)amino.

Dyeing Method in One or More Stages

The method for dyeing keratinous fibres consists in treating, in one or more stages, with one or more cosmetic compositions comprising the following ingredients, taken together or separately in the said composition or compositions:
  a) one or more ortho-diphenol(s) as defined above;
  b) one or more inorganic titanium salt(s) or the alkoxytitanium(s) as defined above;
  c) one or more carboxylic acid(s) of formula (I) as defined above;
  d) optionally, one or more chemical oxidizing agent(s) chosen in particular from hydrogen peroxide or one or more hydrogen peroxide generating system(s);

it being understood that the composition or at least one of the compositions employed in the dyeing method is at acidic pH, i.e. less than 7.0, particularly less than 5, more particularly at a pH of between 0 and 4 inclusive, preferably between 0.5 and 3.5, more preferably between 1 and 3.

According to a specific embodiment of the invention, the dyeing method is carried out in at least two stages which comprise a first stage in which the keratinous fibres are treated with a cosmetic composition comprising a) one or more ortho-diphenol(s) as defined above, b) one or more inorganic titanium salt(s) or the alkoxytitanium(s) as defined above and c) one or more carboxylic acid(s) of formula (I) as defined above, followed by a second stage in which an alkaline cosmetic composition, i.e. the pH of which is greater than 7, preferably between 8 and 12 and in particular between 8 and 10.5, which comprises e) one or more basifying agent(s), is applied.

Preferably, the cosmetic composition applied to the keratinous fibres during the second stage additionally comprises d) one or more chemical oxidizing agent(s) chosen in particular from hydrogen peroxide or one or more hydrogen peroxide generating system(s), preferably hydrogen peroxide.

The leave-in time after application of the composition comprising the ortho-diphenol or ortho-diphenols is generally set at between 3 and 120 minutes, preferably between 10 and 60 minutes and more preferably between 15 and 45 minutes.

According to this specific embodiment of the invention, the method for dyeing keratinous fibres is carried out in two stages by the application, to the keratinous fibres, of a dyeing composition comprising the ingredients a), b) and c) as defined above and then, in a second stage, a composition comprising the ingredient e) and optionally the ingredient d) as defined above is applied to the said keratinous fibres, it being understood that at least one of the two compositions is aqueous. Preferably, the composition comprising the ortho-diphenol(s) a) is aqueous. More preferably still, the two compositions employed in this embodiment are aqueous.

For this dyeing method, the leave-in time after application for the first stage is generally set at between 3 and 120 minutes, preferably between 10 and 60 minutes and more preferably between 15 and 45 minutes. The application time of the composition comprising the ingredient e) during the second stage is generally set at between 3 and 120 minutes, preferably between 3 and 60 minutes and more preferably between 5 and 30 minutes.

According to another embodiment, the method for dyeing keratinous fibres is carried out in two or three stages.

According to one embodiment, the method for dyeing keratinous fibres is carried out in several stages by application to the keratinous fibres, in a first step, of a cosmetic composition comprising:
  a) one or more ortho-diphenol derivative(s) chosen in particular from:
    haematein, brazilein, gallic acid or tannic acid, when the dyeing method does not employ a chemical oxidizing agent d); or else
    haematoxylin or brazilin, when the dyeing method employs a chemical oxidizing agent d);
  b) one or more inorganic titanium salt(s) or the alkoxytitanium(s) as defined above;

c) one or more carboxylic acid(s) of formula (I) as defined above with A representing a monovalent ($C_1$-$C_6$)alkyl or polyvalent ($C_1$-$C_6$)alkylene group optionally substituted by one or more hydroxyl groups, and n representing an integer between 0 and 5, such as between 0 and 2, inclusive; more particularly, the carboxylic acid or acids of the invention are chosen from citric acid, lactic acid, glycolic acid and tartaric acid;

then, in a second stage, the application to the said fibres of a cosmetic composition comprising:

d) optionally one or more chemical oxidizing agent(s) chosen from hydrogen peroxide or one or more hydrogen peroxide generating system(s);

e) one or more basifying agent(s) chosen from alkanolamines and (bi)carbonates, in particular alkali metal or alkaline earth metal (bi)carbonates, preferably (bi)carbonates; it being understood that:

the composition comprising the carboxylic acid or carboxylic acids is at acidic pH, i.e. less than 7, preferably less than 5, in particular at a pH of between 1 and 3 inclusive; and the composition comprising the basifying agent or agents is at alkaline pH, preferably of between 8 and 12 and more particularly of between 8 and 10.

Whatever the form of application, the application temperature is generally between ambient temperature (15° C. to 25° C.) and 220° C. and more particularly between 15° C. and 45° C. Thus, after application of the composition according to the invention, the head of hair can advantageously be subjected to a heat treatment by heating to a temperature of between 30° C. and 60° C. In practice, this operation can be carried out using a styling hood, a hairdryer, an infrared ray dispenser and other conventional heating appliances.

Use may be made, both as means for heating and for smoothing the head of hair, of a heating iron at a temperature of between 60° C. and 220° C. and preferably between 120° C. and 200° C.

Whatever the form of application, it is possible to carry out a rinsing or a mechanical wiping and/or a drying of the keratinous fibres between each stage, in particular before carrying out the final stage comprising the application of a composition comprising the ingredient e).

The stages of intermediate mechanical wiping and drying are also known as "controlled leave-in" to distinguish from "conventional copious rinsing with water" and "leave-in". "Mechanical wiping" of the fibres is understood to mean the rubbing of an absorbent article over the fibres and the physical removal by the absorbent article of the excess ingredient(s) which have not penetrated into the fibres. The absorbent article can be a piece of fabric, such as a towel, particularly a terry cloth, a dish towel or absorbent paper, such as a household roll towel.

According to a particularly advantageous method of the invention, the mechanical wiping is performed without total drying of the fibre, leaving the fibre moist.

Drying is understood to mean the action of evaporating the organic solvents and/or water which occur in one or more compositions used in the method of the invention, comprising or not comprising one or more ingredients a) to e) as defined above. The drying can be carried out with a source of heat (convection, conduction or radiation) by sending out, for example, a stream of hot gas, such as air, necessary for the evaporation of the solvent or solvents. Mention may be made, as source of heat, of a hairdryer, a hairstyling hood, a hair-smoothing iron, an infrared ray dispenser or other conventional heating appliances.

A specific form of the invention relates to a dyeing method which is carried out at ambient temperature (25° C.).

In all the specific and variant forms of the methods described above, the compositions mentioned are ready-for-use compositions which can result from the extemporaneous mixing of two or more than two compositions and in particular of compositions present in dyeing kits.

Dyeing Device or Kit

Another subject-matter of the invention is a multicompartment dyeing device or kit. Advantageously, this kit comprises from 2 to 5 compartments comprising from 2 to 5 compositions in which are distributed the ingredients a) to e) as defined above, which can be aqueous or pulverulent, with in particular at least one of the said compositions being aqueous.

According to a first alternative form, the kit comprises 5 compartments, the first 4 compartments respectively comprising the powdered ingredients a), b), c) and e) as defined above and the $5^{th}$ compartment comprising an aqueous oxidizing composition, such as water comprising d) as defined above.

In this other embodiment, at least one of the four compositions is aqueous and the ortho-diphenol derivative(s) can be in the powder form.

In another kit alternative form, the kit comprises two compartments, in which the first composition present in the first compartment comprises a), b), c) and d) and the $2^{nd}$ compartment comprises e) in the powder form or in aqueous medium; preferably, the second composition is aqueous.

According to one alternative form, the device according to the invention furthermore comprises an additional composition comprising one or more treating agents.

The compositions of the device according to the invention are packaged in separate compartments, optionally accompanied by suitable application means which are identical or different, such as fine brushes, coarse brushes or sponges.

The device mentioned above can also be equipped with a means which makes it possible to dispense the desired mixture on the hair, for example such as the devices described in Patent FR 2 586 913.

Another subject-matter of the invention is the use of the said cosmetic dyeing composition for dyeing keratinous fibres.

Another subject-matter of the invention is the use of one or more carboxylic acid(s) of formula (I) as defined above for improving the colouration of keratinous fibres produced starting from ortho-diphenol(s) in the presence of inorganic titanium salt(s) or in the presence of alkoxytitanium(s).

"Buildup" also called <<uptake>> of the colour of the keratinous fibres is understood to mean, within the meaning of the present invention, the variation in colouration between undyed locks of grey hair and dyed locks of hair.

The following example serves to illustrate the invention without, however, exhibiting a limiting nature.

DYEING EXAMPLES

Example 1

The following compositions are prepared from the following ingredients in the following proportions, indicated in grams:

Dyeing Compositions:

| Ingredients | CAS | Composition 1 | Composition 2 |
|---|---|---|---|
| Pure haematoxylin | 517-28-2 | 4 g | 4 g |
| Ethanol | | 15 g | 15 g |
| Citrate/sodium hydroxide/ hydrogen chloride, buffer pH = 2 (20° C.) Certipur ref. 109433 (Merck) | 7647,-01- Trimethyl-1H- indol-4-amine hydrochloride 7732-18-5 (water) | 46.8 g | 58.3 g |
| Titanium(III) chloride in solution ref. 14010 (Sigma) | 7705-07-9 | 34.2 g | — |
| Titanium(III) sulfate ref. 495182 (Aldrich) | 19495-50-8 | — | 22.7 g |
| Water | | q.s. for 100 g | q.s. for 100 g |

Alkaline Composition B:

| Ingredients | Amount |
|---|---|
| Sodium bicarbonate | 5 g |
| L-Arginine | 7 g |
| Aqueous hydrogen peroxide solution (50%) | 2.4 g |
| Water | q.s. 100 g |
| pH agent | pH 9.2 |

Procedure

Each composition 1 or 2 is applied to locks of natural or permanent-waved Caucasian hair comprising 90% white hairs and locks of natural Chinese hair comprising 100% white hairs, in a proportion of 2 grams of composition per 1 gram of hair. The compositions are subsequently left to stand on the locks for 45 minutes at a temperature of 40° C.

Composition B is subsequently applied to each of the locks in a proportion of 2 grams of composition per one gram of locks. The pH of composition B is 9.2. The leave-in time is 15 minutes at a temperature of 45° C. The locks are subsequently washed with Elseve Multivitamin shampoo, rinsed and then dried under a hood.

The colourations obtained are measured using a Minolta CM-3600D spectrocolorimeter in comparison with undyed hair.

The persistences are also measured using the same spectrocolorimeter in comparison with hair which has not been subjected to a persistence test.

Dyeing Results

The colour of the locks was evaluated in the CIE $L^*$ $a^*$ $b^*$ system using a Minolta Spectrophotometer CM3600D colorimeter. In this $L^*$ $a^*$ $b^*$ system, the three parameters respectively denote the intensity of the colour ($L^*$), the green/red colour axis ($a^*$) and the blue/yellow colour axis ($b^*$).

Buildup of the Colour:

The variation in colouration between the locks of permanent-waved grey hair comprising 90% white hairs (90 PW) or the locks comprising 100% white hairs which are untreated (control) and after treatment or dyeing are defined by ($\Delta E^*$) according to the following equation:

$$\Delta E = \sqrt{(L^* - L_o^*)^2 + (a^* - a_o^*)^2 + (b^* - b_o^*)^2}$$

In this equation, $L^*$, $a^*$ and $b^*$ represent the values measured on locks of hair after dyeing and $L_o^*$, $a_o^*$ and $b_o^*$ represent the values measured on locks of undyed virgin hair. The higher the $\Delta E^*$ value, the better is the buildup of the colour.

| Untreated hair | $L^*$ | $a^*$ | $b^*$ |
|---|---|---|---|
| Natural Caucasian, 90% white hairs | 68.76 | 0.72 | 15.5 |
| Permanent-waved Caucasian, 90% white hairs | 67.38 | 0.76 | 15.03 |
| Natural Chinese, 100% white hairs | 74.92 | 2.4 | 23.92 |

Black locks are obtained which are very intensely coloured, as is shown by the following colorimetric measurements.

| Hair after dyeing | Colour | $L^*$ | $a^*$ | $b^*$ | $\Delta E^*$ buildup |
|---|---|---|---|---|---|
| Composition 1 + B | | | | | |
| Natural Caucasian, 90% white hairs | black | 20.76 | 1.42 | 1.16 | 50.1 |
| Permanent-waved Caucasian, 90% white hairs | black | 20.16 | 1.37 | 0.78 | 49.33 |
| Natural Chinese, 100% white hairs | black | 20.91 | 1.66 | 1.3 | 58.55 |
| Composition 2 + B | | | | | |
| Natural Caucasian, 90% white hairs | black | 21.99 | 0.79 | 1.58 | 48.8 |
| Permanent-waved Caucasian, 90% white hairs | black | 20.1 | 0.59 | 1.32 | 49.23 |
| Natural Chinese, 100% white hairs | grey/black | 26.41 | 1.7 | 4.06 | 52.42 |

Persistence of the Colour

The hair is then subjected to tests of persistence towards light (Xenotest Alpha).

The hair dyed by composition 1+B is subjected in addition to tests of persistence:

towards sweat by immersion at 37° C. in an oven for 48 hours in artificial sweat having composition C.

| Ingredients | Amount |
|---|---|
| Sodium chloride | 10 g |
| Disodium phosphate | 1 g |
| Histidine | 0.25 g |
| Water | q.s. 100 g |
| Lactic acid | q.s. for pH 3.2 | and towards shampoos (Elseve Multivitamin shampoo).

The locks dyed starting from the compositions described above were exposed to light.

The colour of the locks was evaluated, before and after exposure to light, before and after treatment with sweat or before and after successive shampooing operations, in the $L^*$ $a^*$ $b^*$ system, by means of a spectrophotometer as defined above.

The variation in the colouring of the locks, before and after exposure to light, before and after treatment with sweat or before and after successive shampooing operations, is measured by $\Delta E'$ according to the following equation:

$$\Delta E' = \sqrt{(L'^* - L_o^*)^2 + (a'^* - a_o^*)^2 + (b'^* - b_o^*)^2}$$

In this equation, $L'^*$, $a'^*$ and $b'^*$ represent the values measured after external treatment of the locks (exposure to light, sweat or successive shampooing operations) and $L_0^*$, $a_0^*$ and $b_0^*$ represent the values measured before exposure.

The greater the ΔE' value, the greater the difference in colour of the lock before and after external treatment, which shows a reduced persistence towards light.

The results in terms of persistence are collated in the following table:

| Hair | Light exposure (40 h Xenotest) % loss/ unexposed hair | Artificial sweat (48 h, 37° C.) % loss/ unexposed hair | After 10 shampooing operations % loss/ unwashed hair |
|---|---|---|---|
| Composition 1 + B | | | |
| Natural Caucasian, 90% white hairs | 3.61 | — | 1.92 |
| Permanent-waved Caucasian, 90% white hairs | 3.47 | 9.12 | 2.06 |
| Natural Chinese, 100% white hairs | 5.19 | — | 3.85 |
| Composition 2 + B | | | |
| Natural Caucasian, 90% white hairs | 7.30 | — | — |
| Permanent-waved Caucasian, 90% white hairs | 3.55 | — | — |
| Natural Chinese, 100% white hairs | 7.31 | — | — |

It is seen that the hair dyed according to the invention exhibits a very good level of persistence which is confirmed by the colorimetric values (very low percentages of losses in ΔE'* with respect to hair which has not been subjected to the persistence test).

Example 2

The following compositions are prepared from the following ingredients in the following proportions, indicated in grams:

Dyeing Composition:

| Ingredients | Composition 3 Invention | Composition 4 Comparative |
|---|---|---|
| Logwood extract comprising 76% of haematoxylin | 4 g | 4 g |
| Ethanol | 15 g | 15 g |
| Benzyl alcohol | 5 g | 5 g |
| Titanium(IV) sulfate as a 15% solution, sold under the name 10326250 by Fisher Chemical (CAS 13693-11-3) | 28 g | 28 g |
| Sodium glycolate | 13 g | — |
| Water | q.s. 100 g | q.s. 100 g |
| pH agent | q.s. for pH = 2.8 ± 0.2 | q.s. for pH = 2.8 ± 0.2 |

Developing Composition:

| Ingredients | Composition B |
|---|---|
| Sodium bicarbonate | 5 g |
| L-Arginine | 7 g |
| Aqueous hydrogen peroxide solution (50%) | 1.7 g |
| Thickener | q.s. for |
| Water | q.s. 100 g |
| pH agent | pH 9.9 |

Locks of natural and permanent-waved Caucasian hair comprising 90% white hairs and locks of natural Chinese hair comprising 100% white hairs are successively treated with composition 3 or 4, which is left to stand at 40° C. for 45 minutes and then wrung out, and with composition B, which is then left to stand at 40° C. for 15 minutes, in a proportion of 2 grams of each of the compositions per gram of hair.

On conclusion of these leave-in times, the locks are washed with Elseve Multivitamin shampoo, rinsed and then dried under a hood.

It is found visually that locks which are intensely coloured black are obtained with composition 3 according to the invention whereas the locks are very weakly coloured with comparative composition 4. This is corroborated with the colorimetric results below:

| Untreated hair | L* | a* | b* |
|---|---|---|---|
| Natural Caucasian, 90% white hairs | 66.48 | 0.5 | 15.14 |
| Permanent-waved Caucasian, 90% white hairs | 66.3 | 0.53 | 14.31 |
| Natural Chinese, 100% white hairs | 77.4 | 2.12 | 23.99 |

| Hair after dyeing | Colour | L* | a* | b* | ΔE* buildup |
|---|---|---|---|---|---|
| Composition 3 + B | | | | | |
| Natural Caucasian, 90% white hairs | black | 22.96 | 0.99 | 0.26 | 46 |
| Permanent-waved Caucasian, 90% white hairs | black | 20.03 | 0.65 | 0.65 | 48.25 |
| Natural Chinese, 100% white hairs | black | 23.55 | 0.8 | 0.04 | 58.95 |
| Composition 4 + B | | | | | |
| Natural Caucasian, 90% white hairs | white | 53.99 | 3.24 | 8.97 | 14.2 |
| Permanent-waved Caucasian, 90% white hairs | grey | 41.39 | 4.36 | 9.75 | 25.61 |
| Natural Chinese, 100% white hairs | white | 59.67 | 3.17 | 11.69 | 21.6 |

The invention claimed is:

1. A method for dyeing keratinous fibers, the method comprising:
    applying to the fibers:
    a) a first composition comprising at least one ortho-diphenol;
    b) a second composition comprising at least one inorganic titanium salt or alkoxytitanium;
    c) a third composition comprising at least one carboxylic acid chosen from those of formula (I) below or salts thereof:

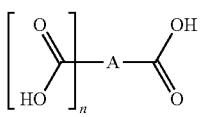

wherein:
A is chosen from a saturated or unsaturated, cyclic or non-cyclic and aromatic or non-aromatic hydrocarbon group, monovalent when n is zero or polyvalent when n is greater than or equal to 1, comprising from 1 to 50 carbon atoms which is optionally interrupted with at least one heteroatom and/or optionally substituted; or a monovalent ($C_1$-$C_6$)alkyl group or a polyvalent ($C_1$-$C_6$)alkylene group optionally substituted with at least one hydroxyl group; and
n is an integer ranging from 0 to 10; and
d) optionally, a fourth composition comprising at least one chemical oxidizing agent;
wherein at least one composition chosen from the first composition, the second composition, the third composition, or the fourth composition has an acidic pH.

2. The method according to claim 1, wherein the at least one ortho-diphenol comprises an aromatic ring chosen from benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline, or isoquinoline, wherein the aromatic ring comprises at least two hydroxyl groups carried by two contiguous adjacent atoms of the aromatic ring.

3. The method according to claim 1, wherein the at least one ortho-diphenol chosen from those of formula (II) below, or oligomers, tautomers, optical isomers, geometrical isomers, salts, solvates, or hydrates thereof:

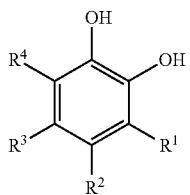

wherein:
$R^1$ to $R^4$, which are identical or different, are chosen from: i) hydrogen, ii) halogen atoms, iii) hydroxyl groups, iv) carboxyl groups, v) ($C_1$-$C_{20}$)alkyl carboxylate or ($C_1$-$C_{20}$)alkoxycarbonyl groups, vi) optionally substituted amino groups, vii) optionally substituted linear or branched ($C_1$-$C_{20}$)alkyl groups, viii) optionally substituted linear or branched ($C_2$-$C_{20}$)alkeny groups, ix) optionally substituted cycloalkyl groups, x) ($C_1$-$C_{20}$) alkoxy groups, xi) ($C_1$-$C_{20}$)alkoxy($C_1$-$C_{20}$)alkyl groups, xii) ($C_1$-$C_{20}$)alkoxyaryl groups, xiii) aryl groups which can optionally be substituted, xiv) aryl groups, xv) substituted aryl groups, xvi) heterocyclic groups which are saturated or unsaturated, optionally bearing a cationic or anionic charge and which are optionally substituted and/or optionally condensed with an aromatic ring, the aromatic ring optionally substituted, or xvii) radical groups comprising at least one silicon atom; or or, optionally:
two of the substituents carried by two adjacent carbon atoms $R^1$-$R^2$, $R^2$-$R^3$ or $R^3$-$R^4$ optionally form, together with the carbon atoms carrying them, a saturated or unsaturated, aromatic or non-aromatic ring optionally comprising at least one heteroatom and optionally fused with at least one saturated or unsaturated ring optionally comprising at least one heteroatom; or
$R^1$ to $R^4$ together form from one to four rings; or
$R^2$ and $R^3$ form a pyrrolyl or pyrrolidinyl radical fused to the benzene ring carrying the two hydroxyls.

4. The method according to claim 1, wherein the at least one ortho-diphenol derivative is chosen from:
flavanols, catechin, epicatechin gallate, or quercetin;
anthocyanidins, cyanidin, delphinidin, or petunidin;
anthocyanins, anthocyans, or myrtillin;
ortho-hydroxybenzoates or gallic acid salts;
flavones or luteolin;
hydroxystilbenes or 3,3',4,5'-tetrahydroxystilbene, optionally oxylated (for example glucosylated);
3,4-dihydroxyphenylalanine or derivatives thereof;
2,3-dihydroxyphenylalanine or derivatives thereof;
4,5-dihydroxyphenylalanine or derivatives;
dihydroxycinnamates, caffeic acid, or chlorogenic acid;
ortho-polyhydroxycoumarins;
ortho-polyhydroxyisocoumarins;
ortho-polyhydroxycoumarones;
ortho-polyhydroxyisocoumarones;
ortho-polyhydroxychalcones;
ortho-polyhydroxychromones;
quinones;
hydroxyxanthones;
1,2-dihydroxybenzene or derivatives thereof;
1,2,4-trihydroxybenzene or derivatives thereof;
1,2,3-trihydroxybenzene or derivatives thereof;
2,4,5-trihydroxytoluene or derivatives thereof;
proanthocyanidins, proanthocyanidins A1, A2, B1, B2, B3, or C1,
chroman or chromene;
proanthocyanins;
tannic acid;
ellagic acid;
haematein;
brazilin;
brazilein;
gallic acid;
tannic acid;
haematoxylin; or
mixtures thereof.

5. The method according to claim 1, wherein the at least one ortho-diphenol derivative is chosen from extracts of animals, bacteria, fungi, algae, plants, or fruit.

6. The method according to claim 1, wherein the at least one ortho-diphenol derivative is chosen from haematoxylin, brazilin, gallic acid, tannic acid, haematein, or brazilein.

7. The method according to claim 1, wherein the at least one carboxylic acid is chosen from compounds of formula (I) wherein A is chosen from a monovalent ($C_1$-$C_6$)alkyl or polyvalent ($C_1$-$C_6$)alkylene group optionally substituted with at least one hydroxyl group, and n is an integer ranging from 0 to 5; citric acid, lactic acid, tartaric acid; or glycolic acid.

8. The method according to claim 1, in which the at least one carboxylic acid is present in an amount ranging from about 0.1% to about 20% by weight, relative to the total weight of the composition.

9. The method according to claim 1, wherein the at least one inorganic titanium salt or alkoxytitanium is chosen from inorganic salts, titanium halides, titanium sulfates, and/or titanium phosphates.

10. The method according to claim 1, wherein the at least one inorganic titanium salt or alkoxytitanium has an oxidation state of 2 or Ti(II), 3 or Ti(III) or 4 or Ti(IV).

11. The method according to claim 1, wherein the at least one inorganic titanium salt or alkoxytitanium is chosen from alkoxytitaniums, wherein the alkoxytitaniums may correspond to the formula $Ti(OR)_n$, wherein n is equal to 2, 3 or 4, and R is chosen from a linear or branched $(C_1-C_{10})$alkyl or $(C_2-C_{10})$alkenyl group optionally substituted with at least one atom or group chosen from halo, hydroxyl, or $(di)(C_1-C_4)(alkyl)$amino.

12. The method according to claim 1, further comprising applying a composition comprising at least one chemical oxidizing agent chosen from hydrogen peroxide, at least one hydrogen peroxide generating system, or urea hydrogen peroxide.

13. The method according to claim 1, further comprising applying at least one basifying agent chosen from i) (bi) carbonates, ii) aqueous ammonia, iii) alkanolamines, monoethanolamine, diethanolamine, triethanolamine, or derivatives thereof, iv) oxyethylenated and/or oxypropylenated ethylenediamines, v) inorganic or organic hydroxides, vi) alkali metal silicates or sodium metasilicates, vii) amino acids, basic amino acids, arginine, lysine, ornithine, citrulline, or histidine; viii) the compounds of formula (V) below:

(V)

wherein:
W is chosen from a divalent $(C_1-C_8)$alkylene radical optionally substituted with at least one hydroxyl group, or at least one $(C_1-C_4)$alkyl radical optionally interrupted with at least one heteroatom, oxygen, sulfur, or $-N(R_e)-$ group; and $R_a$, $R_b$, $R_c$, $R_d$ and $R_e$, which may be identical or different, are chosen from a hydrogen atom, $(C_1-C_4)$alkyl radicals, hydroxy$(C_1-C_4)$alkyl radicals, propylene radicals, or mixtures thereof.

14. The method according to claim 1, wherein the at least one of the first composition, the second composition, the third composition, and/or the fourth composition further comprise at least one organic solvent chosen from lower $C_1-C_4$ alkanols, ethanol, isopropanol, polyols, polyol ethers, 2-butoxyethanol, propylene glycol, propylene glycol monomethyl ether, diethylene glycol monoethyl ether, diethylene glycol monomethyl ether, hexylene glycol, aromatic alcohols, benzyl alcohol, phenoxyethanol, aromatic alcohols, benzyl alcohol, or mixtures thereof.

15. The method according to claim 1, comprising:
applying to the keratin fibers the first composition, the second composition, and the third composition to form treated keratin fibers; and
applying to the treated keratin fibers an alkaline composition, comprising:
at least one basifying agent, and;
optionally, at least one chemical oxidizing agent chosen from hydrogen peroxide or at least one hydrogen peroxide generating system.

16. The method according to claim 15, wherein:
the at least one ortho-diphenol derivative is chosen from haematein, brazilein, gallic acid or tannic acid, when the method does not comprise applying a chemical oxidizing agent; or haematoxylin or brazilin, when the method does comprise applying a chemical oxidizing agent;
the at least one inorganic titanium salt or alkoxytitanium is chosen from Ti(III) or Ti(IV) salts or compounds;
the at least one carboxylic acid is chosen from compounds corresponding to formula (I) wherein A is chosen from a monovalent $(C_1-C_6)$alkyl or polyvalent $(C_1-C_6)$alkylene group optionally substituted with at least one hydroxyl group, and n is an integer ranging from 0 to 5, citric acid, or lactic acid;
the at least one chemical oxidizing agent is chosen from hydrogen peroxide or at least one hydrogen peroxide generating system;
the at least one basifying agent is chosen from alkanolamines, (bi)carbonates, alkali metal, or alkaline earth metal (bi)carbonates;
the composition comprising the at least one carboxylic acid has an acidic pH; and
the composition comprising the at least one basifying agent has an alkaline pH.

17. A cosmetic composition for dyeing keratinous fibers, comprising:
a) at least one ortho-diphenol;
b) at least one inorganic titanium salt or alkoxytitanium;
c) at least one carboxylic acid represented by formula (I) below or salts thereof:

(I)

wherein:
A is chosen from a saturated or unsaturated, cyclic or non-cyclic and aromatic or non-aromatic hydrocarbon group, monovalent when n is zero or polyvalent when n is greater than or equal to 1, comprising from 1 to 50 carbon atoms which is optionally interrupted with at least one heteroatom and/or optionally substituted; or a monovalent $(C_1-C_6)$alkyl group or a polyvalent $(C_1-C_6)$alkylene group optionally substituted with at least one hydroxyl group; and
n is an integer ranging from 0 to 10;
d) optionally, a fourth composition comprising at least one chemical oxidizing agent;
e) optionally, a fifth composition comprising at least one basifying agent chosen from alkanolamines, (bi)carbonates, alkali metal, or alkaline earth metal (bi)carbonates; and
f) optionally, at least one organic solvent chosen from lower $C_1-C_4$ alkanols, ethanol, isopropanol, polyols, polyol ethers, 2-butoxyethanol, propylene glycol, propylene glycol monomethyl ether, diethylene glycol monoethyl ether, diethylene glycol monomethyl ether, hexylene glycol, aromatic alcohols, benzyl alcohol, phenoxyethanol, aromatic alcohols, benzyl alcohol, or mixtures thereof;

wherein at least one composition chosen from the first composition, the second composition, the third composition, the fourth composition, and/or the fifth composition has an acidic pH.

18. A multicompartment device comprising from 2 to 5 compartments containing from 2 to 5 compositions, the device comprising:
   a) a first composition comprising at least one ortho-diphenol;
   b) a second composition comprising at least one inorganic titanium salt or alkoxytitanium;
   c) a third composition comprising at least one carboxylic acid chosen from those of formula (I) below, or salts thereof:

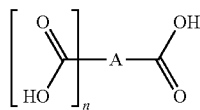 (I)

wherein:
   A is chosen from a saturated or unsaturated, cyclic or non-cyclic and aromatic or non-aromatic hydrocarbon group, monovalent when n is zero or polyvalent when n is greater than or equal to 1, comprising from 1 to 50 carbon atoms which is optionally interrupted with at least one heteroatom and/or optionally substituted; or a monovalent $(C_1\text{-}C_6)$alkyl group or a polyvalent $(C_1\text{-}C_6)$alkylene group optionally substituted with at least one hydroxyl group; and
   n is an integer ranging from 0 to 10; and
   d) optionally, a fourth composition comprising at least one chemical oxidizing agent; and
   e) optionally, a fifth composition comprising at least one basifying agent chosen from alkanolamines, (bi)carbonates, alkali metal, or alkaline earth metal (bi)carbonates;

wherein at least one composition chosen from the first composition, the second composition, the third composition, the fourth composition, and/or the fifth composition has an acidic pH; and wherein the first composition, the second composition, the third composition, the fourth composition, and/or the fifth composition are aqueous or pulverulent.

* * * * *